United States Patent
Prevrhal et al.

(10) Patent No.: US 12,347,000 B2
(45) Date of Patent: Jul. 1, 2025

(54) APPARATUS, SYSTEM, METHOD AND COMPUTER PROGRAM FOR PROVIDING A NUCLEAR IMAGE OF A REGION OF INTEREST OF A PATIENT

(71) Applicant: KONINKLIJKE PHILIPS N.V., Eindhoven (NL)

(72) Inventors: Sven Peter Prevrhal, Hamburg (DE); Michael Grass, Buchholz In der Nordheide (DE); Andreas Georg Goedicke, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 396 days.

(21) Appl. No.: 17/786,616

(22) PCT Filed: Dec. 18, 2020

(86) PCT No.: PCT/EP2020/087297
§ 371 (c)(1),
(2) Date: Jun. 17, 2022

(87) PCT Pub. No.: WO2021/123364
PCT Pub. Date: Jun. 24, 2021

(65) Prior Publication Data
US 2023/0022425 A1    Jan. 26, 2023

(30) Foreign Application Priority Data
Dec. 19, 2019   (EP) .................................... 19218131

(51) Int. Cl.
*G06T 11/00* (2006.01)
*A61B 6/00* (2006.01)
*A61B 6/03* (2006.01)

(52) U.S. Cl.
CPC ............ *G06T 11/008* (2013.01); *A61B 6/037* (2013.01); *A61B 6/527* (2013.01); *G06T 2210/41* (2013.01)

(58) Field of Classification Search
CPC . G06T 11/008; G06T 2210/41; G06T 11/005; G06T 2211/12; G06T 11/003;
(Continued)

(56) References Cited

U.S. PATENT DOCUMENTS

2009/0225933 A1   9/2009  Shao
2012/0078089 A1*  3/2012  Wollenweber ....... A61B 6/5258
                                                250/363.03
(Continued)

FOREIGN PATENT DOCUMENTS

CN      104884126 B  *  8/2018  ............. A61B 34/30
JP         4439022 B2 *  3/2010
WO      2018172229 A1    9/2018

OTHER PUBLICATIONS

International Search Report and Written Opinion of PCT/EP2020/087297, dated Feb. 8, 2021.
(Continued)

*Primary Examiner* — Jose L Couso

(57) ABSTRACT

The invention refers to an apparatus that allows to improve the image quality of nuclear images, e.g. PET images. The apparatus (110) comprises a providing unit (111) for providing nuclear image data of a region of interest, a providing unit (112) for providing a motion signal indicative of a motion of the region of interest, a determination unit (113) for determining different motion states of the region of interest based on the motion signal, a determination unit (114) for determining for each motion state nuclear image data corresponding to the motion state, a reconstruction unit (115) for reconstructing an absorption map for each motion state based on the corresponding nuclear image data of the
(Continued)

respective motion state, and a reconstruction unit (116) for reconstructing one or more nuclear images of the region of interest based on the nuclear image data and the absorption maps reconstructed for each motion state.

21 Claims, 3 Drawing Sheets

(58) Field of Classification Search
CPC ......... G06T 7/0012; G06T 2207/10104; G06T 2207/10108; G06T 2207/10116; G06T 2207/10124; G06T 2207/30004; G06T 2211/416; G06T 5/50; G06T 7/014; G06T 7/11; G06T 5/00; G06T 2211/464; G06T 2211/412; G06T 3/4046; G06T 5/60; G06T 9/002; G06T 2207/20076; G06T 2207/20081; G06T 2207/20084; A61B 6/037; A61B 6/527; A61B 6/5288; A61B 6/5264; A61B 6/032; A61B 6/5205; A61B 6/5235; A61B 6/5258; A61B 6/5247; A61B 6/469; A61B 5/08; A61B 8/08; A61B 8/463; A61B 8/483; A61N 2205/1052; A61N 5/1037; A61N 5/1039; A61N 5/1049; A61N 5/1067; G01T 1/1611; G06N 3/02; G06N 3/08–088; G06N 3/0445; G06N 3/0454; G06N 3/4046; G06N 7/00; G06N 7/01; G06N 20/00; G06K 7/1482; G06V 10/454; G06V 10/54; G06V 10/774; G06V 10/82; G06V 30/18057; G06F 18/214; G06F 18/22; G06F 18/241; G06F 18/2415; Y10S 128/925

See application file for complete search history.

(56) References Cited

U.S. PATENT DOCUMENTS

| | | |
|---|---|---|
| 2013/0287278 A1 | 10/2013 | Olivier |
| 2015/0221104 A1* | 8/2015 | Ra .................. G06T 11/005 382/131 |
| 2018/0353147 A1 | 12/2018 | Wang |
| 2019/0130569 A1 | 5/2019 | Liu |
| 2019/0133542 A1* | 5/2019 | Li .................. A61B 6/5247 |
| 2020/0000424 A1* | 1/2020 | Spottiswoode ...... A61B 6/5264 |

OTHER PUBLICATIONS

Salomon, A. et al "Robust Real-Time Extraction of Respiratory Signals from PET List-Mode Data", Physics in Medicine and Biolody, vol. 63, No. 11, 2018.

Bai, Wenjia et al Motion Correction and Attenuation Correction for Respiratory Gated PET Images, IEEE Transactions on Medical Imaging, vol. 30, No. 2, Feb. 2011, pp. 351-365.

Zaidi, Habib et al "Advances in Attenuation Correction Techniques in PET", Positron Emission Tomography, PET Clinics, vol. 2, No. 2, Apr. 2007, pp. 191-217.

* cited by examiner

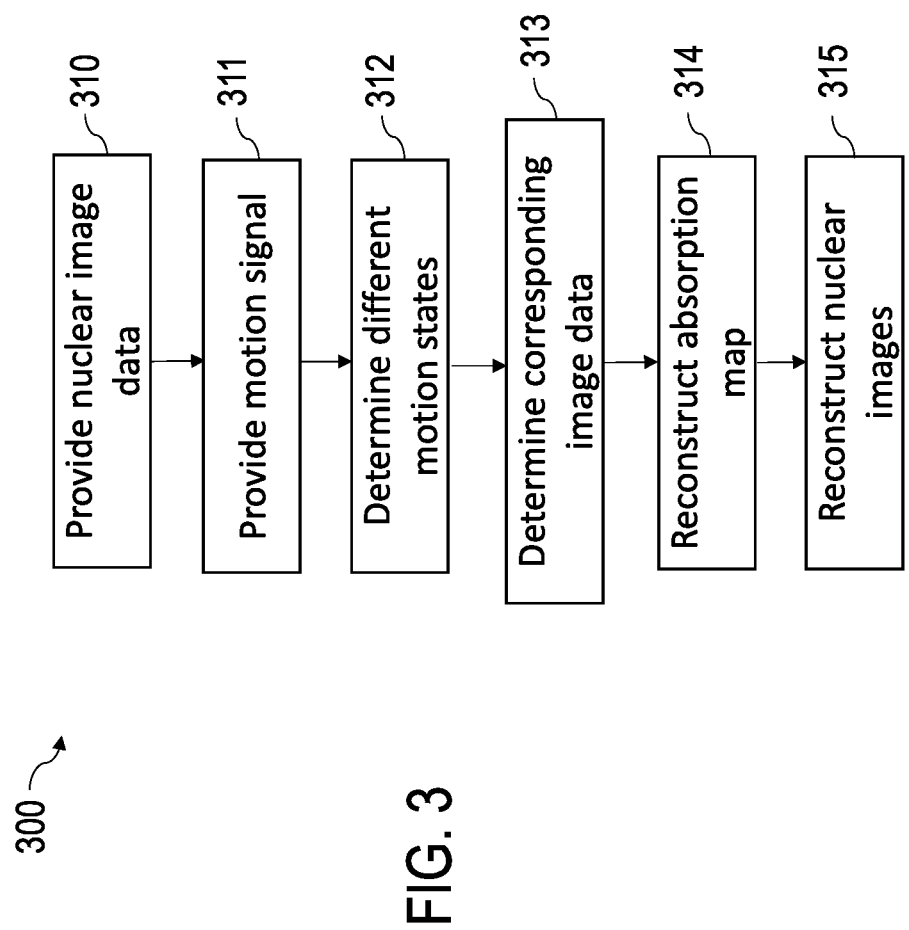

APPARATUS, SYSTEM, METHOD AND COMPUTER PROGRAM FOR PROVIDING A NUCLEAR IMAGE OF A REGION OF INTEREST OF A PATIENT

CROSS-REFERENCE TO PRIOR APPLICATIONS

This application is the U.S. National Phase application under 35 U.S.C. § 371 of International Application No. PCT/EP2020/087297, filed on Dec. 18, 2020, which claims the benefit of European Patent Application No. 19218131.1, filed on Dec. 19, 2019. These applications are hereby incorporated by reference herein.

FIELD OF THE INVENTION

The invention relates to an apparatus, a system, a method and a computer program for providing a nuclear image of a region of interest of a patient.

BACKGROUND OF THE INVENTION

Nuclear image data acquisition, for instance, using a PET imaging system, is generally very time-consuming, i.e. to detect the necessary amount of events, the image data is acquired during an extended time period. Thus, during such an extended time period, body motions of a patient, for instance, breathing motions or other involuntary motions, cannot be completely avoided. Reconstructing a nuclear image based on the nuclear image data, which has been acquired during a movement of the patient, leads to a low quality of the resulting nuclear image. The common approach to correcting the nuclear image data for breathing motion is to provide 4D CT image data in addition to the nuclear image data. The 4D CT image data refers to CT image data that has been acquired during at least one breathing cycle of the patient. Since CT image data can be acquired very fast, the 4D CT image data maps the breathing motion of the patient very accurately. In this approach, the nuclear image data is then sorted in accordance to different breathing states, for instance, using a breathing sensor, and registered to the 4D CT image data. This allows to correct for the attenuation of the nuclear image data and also to correct for motion in the nuclear image data. However, since the 4D CT image data is acquired only for a very short time period, whereas the nuclear image data is acquired during a much longer time period, irregularities in the motion of the patient, for instance, in the breathing pattern or other irregular involuntary motions, will not be represented by the 4D CT image data and thus will still lead to artifacts and inaccuracies in the reconstruction of the nuclear image. An alternative possibility to avoid the influence of motion, for instance, breathing motion, in nuclear imaging is to use an external breathing sensor and to gate the acquisition of the nuclear image data according to the signal of the external breathing sensor, i.e. to acquire only nuclear image data during one breathing state in the breathing cycle of the patient. However, this kind of acquisition leads to an increased acquisition time until the needed amount of events has been detected by the nuclear imaging system. In many cases, due to the discomfort of the patient during the nuclear image data acquisition, an increase in acquisition time is not acceptable.

SUMMARY OF THE INVENTION

It is an object of the present invention to provide an apparatus, a system, a method and a computer program that allow to improve the image quality of nuclear images without increasing the discomfort for a patient.

In a first aspect of the invention, an apparatus for providing a nuclear image of a region of interest of a patient is presented, wherein the apparatus comprises a) a nuclear image data providing unit for providing nuclear image data of a region of interest of a patient acquired using a nuclear imaging device, b) a motion signal providing unit for providing a motion signal indicative of a motion of the region of interest of the patient during an acquisition of the nuclear image data, c) a motion state determination unit for determining different motion states of the region of interest based on the motion signal, wherein each of the different motion states is indicative for a different state of the region of interest, d) a corresponding image data determination unit for determining for each motion state nuclear image data corresponding to the motion state, wherein nuclear image data corresponds to a motion state if the nuclear image data has been acquired during a state of the region of interest corresponding to the motion state, e) an absorption map reconstruction unit for reconstructing an absorption map for each motion state based on the corresponding nuclear image data of the respective motion state, wherein the absorption map is indicative of an absorption of nuclear radiation in the region of interest, and f) a nuclear image reconstruction unit for reconstructing one or more nuclear images of the region of interest based on the nuclear image data and the absorption maps reconstructed for each motion state.

Since the corresponding image data determination unit determines for each motion state nuclear image data corresponding to a motion state and the absorption map reconstruction unit reconstructs an absorption map for each motion state based on the corresponding nuclear image data of the respective motion state, the reconstructed absorption maps are determined from the same nuclear image data which should later be used for reconstructing the nuclear image and can be regarded as corresponding to the same time period in which the nuclear image has been acquired. Thus, the absorption maps reflect the motion of the patient during the acquisition of the nuclear image data very accurately. Since the nuclear image reconstruction unit then reconstructs one or more nuclear images of the region of interest based on the nuclear image data and the absorption maps reflect the motion of the patient during the acquisition period very accurately, the motion in the nuclear images can be corrected very accurately. Moreover, also the attenuation correction is improved due to a high conformity between the nuclear image data and the absorption maps that are reconstructed from the nuclear image data. Therefore, the image quality of a reconstructed nuclear image can be improved without an extension of the nuclear image data acquisition and thus without leading to further discomfort for the patient.

The nuclear image data providing unit is adapted to provide nuclear image data of a region of interest of a patient acquired using a nuclear imaging device. The nuclear image data providing unit can be a storing unit in which the nuclear image data is stored already and from which the nuclear image data can be retrieved. Also, the nuclear image data providing unit can be a retrieving unit for retrieving the nuclear image data from, for instance, a nuclear imaging system that is used for acquiring the nuclear image data, wherein the nuclear image data providing unit is then adapted to provide the acquired nuclear image data.

The provided nuclear image data can refer to any kind of nuclear image data that has been acquired using a nuclear imaging system. The nuclear imaging system refers to an imaging system that uses detectors for detecting radiation that has been emitted from at least one region of interest within the body of a patient. In particular, a nuclear imaging system does not refer to a system that acquires radiation that is transmitted through the body of the patient, for instance, by providing a radiation source outside of the body of the patient like in X-ray CT imaging. The nuclear imaging system used for acquiring the nuclear image data can refer, for instance, to a PET imaging system, a SPECT imaging system, etc. The nuclear image data can thus refer to PET image data, SPECT image data, etc.

The motion signal providing unit is adapted to provide a motion signal indicative of a motion of the region of interest of the patient during the acquisition of the nuclear image data. The motion signal providing unit can be a storing unit for storing the motion signal and from which the motion signal can be retrieved. Also, the motion signal providing unit can be a retrieving unit for retrieving the motion signal, for instance, from a motion sensor which has acquired the motion signal during the acquisition of the nuclear image data. The motion signal can be any signal that is indicative of motion in the region of interest during the acquisition of the nuclear image data. For instance, the motion signal can be a 1D signal recording a position or acceleration of one point in the region of interest with time. However, the motion signal can also be a 2D or 3D signal recording a position or acceleration of more than one position in the region of interest with time. For example, the motion signal can also refer to a motion map, like a vector map, indicating the motion of each part, like each pixel or voxel, of the region of interest with time.

In an embodiment, the motion signal providing unit is adapted to provide as motion signal a signal of a sensor configured to detect a motion of the region of interest of the patient. For instance, the motion signal can be acquired by using a motion sensor that is attached to the region of interest of the patient and that measures the motion of the region of interest of the patient during the acquisition of the nuclear image data. Alternatively, the motion signal providing unit can be adapted to extract a motion signal indicative of a motion in the region of interest of a patient from a monitoring camera monitoring the patient during the acquisition of the nuclear image data. In this embodiment, known motion extraction and tracking methods for monitoring images can be used for extracting the motion signal from the monitoring images.

In a preferred embodiment, the motion signal providing unit can be adapted to determine the motion signal based on the nuclear image data. For instance, the motion signal providing unit can be adapted to determine the motion signal directly from the nuclear imaging data by using the time of flight information provided in the nuclear image data. A general outline of an exemplary method for determining motion from nuclear image data is provided in the article "Robust real-time extraction of respiratory signals from PET list-mode data" by A. Salomon et al., Physics in Medicine & Biology, volume 63, number 11 (2018). However, also other methods can be used for extracting a motion signal, i.e. a signal indicative of motion of a region of interest of a patient, from the nuclear image data itself. Extracting the motion signal from the nuclear image data itself has the advantage that no additional motion sensing unit, like a camera or a dedicated motion sensor, has to be provided during the nuclear imaging. Moreover, even nuclear image data that has been acquired completely without the additional detection of a motion signal, or for which a provided motion signal has been corrupted, can thus be processed.

The motion signal can refer to a specific motion signal, for instance, to a motion signal that is indicative of only one kind of motion, like breathing motion, or to a general motion signal that is indicative of all motions of the patient in the region of interest, for instance, also of non-regular motions that are not part of the general cyclic motions of the patient, like breathing or heart movement. In another preferred embodiment, the motion signal is indicative for the entire spatial motion pattern of the region of interest. This can be achieved, for instance, if the motion signal providing unit is adapted to determine the motion signal from the nuclear image data itself. In other embodiments, the motion signal can also be indicative for heart motion, bowel motion or any other motions of the patient during the acquisition of the nuclear image data. In another preferred embodiment, the motion signal is indicative of a regular body motion of the region of interest of the patient. In particular, the motion signal can be indicative of a cyclic motion of the region of interest. In a preferred embodiment, the motion signal is indicative for the breathing motion of the patient.

The motion state determination unit is adapted to determine different motion states of the region of interest based on the motion signal. Each of the different motion states is indicative of a different state of the region of interest. A different state of the region of interest refers, for instance, to different positions or forms of anatomical structures in the region of interest. Possible motion states for the region of interest can be predetermined, for instance, based on a user input or based on pre-knowledge on the region of interest. The motion state determination unit can then be adapted to determine which of the possible motion states can be found during the acquisition of the nuclear image data based on the motion signal. Moreover, the motion state determination unit can be adapted to automatically determine motion states, for instance, by searching for specific characteristics in the motion signal, like local maxima, local minima, or substantially constant time periods in the motion signal and defining the state of the region of interest during which these motion signal characteristics have been acquired as motion state.

Further, if at least two motion states have been determine based on the motion signal, motion states between these two already determined motion states can also be determined by the motion state determination unit by interpolating between these two motion states to acquire a third motion state between the two motion states. The interpolation can, for instance, refer to defining a motion state halfway between the two motion states. In this case, for instance, only a few motion states have to be determined directly from the motion signal, while other motion states can then be determined based on the already determined motion states.

Preferably, the different motion states refer to different substantially motionless states of the region of interest. In particular, the motion state determination unit can be adapted to differentiate from the motion signal time periods during the acquisition of the motion signal at which the region of interest of the patient was substantially motionless. In this context a substantially motionless state of a region of interest can be defined as a state in which the region of interest or parts of the region of interest show motion below a predetermined threshold within a certain time period. The threshold can be determined, for instance, based on the region of interest and on the accuracy that should be achieved by the imaging procedure. For instance, if the region of interest refers to a region of interest in which not many motions occur and/or if a tumor that should be imaged by the nuclear imaging is expected to be very small, the threshold can be determined smaller than if it is known that in the region of interest many involuntary motions occur and/or if the tumor that should be imaged is expected to be large. Generally, the threshold can be chosen such that the motions of the region of interest in the substantially motionless state are still acceptable for a user and for the planned application of the resulting nuclear image.

A time period during which the region of interest has to show movement below the predetermined threshold can be predetermined or can be adaptable during the determination of the motion states. For instance, the motion state determination unit can be adapted to identify the motion states based on a shortest time period threshold. The shortest time period threshold refers to the shortest time period for which a motion state should be determined. The shortest time period threshold can be determined based on the provided motion signal accuracy or based on the accuracy that should be provided by the resulting nuclear image. The motion state determination unit can then be adapted to determine a state of the body of the patient as motion state if during a time period longer than the shortest time period threshold the region of interest of the patient is substantially motionless. For instance, if the motion signal indicates in some time period that the patient is moving fast, i.e. the region of interest shows a high rate of change during a short time period, the motion state determination unit can be adapted to determine more motion states for this time period than during time periods in which the motion signal indicates that the region of interest is moving slowly, i.e. shows only small changes during long time periods.

If the motion signal indicates that the motion in the region of interest is a regular periodic or cyclic motion, the motion state determination unit can be adapted to determine the same motion states for each period or cycle of the periodic or cyclic motion. For instance, if the motion signal is indicative of a breathing motion of a patient, the motion state determination unit can be adapted to determine as a first motion state a state of the region of interest referring to an exhalation state and as a second motion state a state of the patient referring to an inhalation state of the patient. These two states can also be regarded as substantially motionless states for a certain time period.

In an embodiment, the motion state determination unit can be adapted to determine the motion states based on an input of the user. For instance, a user can indicate in a representation of the motion signal where the motion signal indicates a motion state. Moreover, the motion state determination unit can also be adapted to determine the motion states based on stored motion states of previous, in particular, similar cases. Moreover, the motion state determination unit can also be a motion state providing unit for providing the motion states based on already stored motion states or based on an input of the user.

The corresponding image data determination unit is adapted to determine for each motion state nuclear image data corresponding to the motion state. The nuclear image data corresponds to a motion state if the nuclear image data has been acquired during a state of the region of interest corresponding to the motion state. For instance, if the motion state is an exhalation state of the patient, i.e. a state in which the lung of the patient is maximally contracted, all nuclear image data having been acquired during such a state of the lung can be determined by the corresponding image data determination unit as corresponding image data. More generally, the image data determination unit can be adapted to determine a time at which a part of the nuclear image data has been acquired and to determine in which of the motion states that has been determined by the motion state determination unit the patient was at the time the part of the nuclear image data has been acquired. This part of the nuclear image data can then be regarded as corresponding to this respective motion state. Preferably, if the nuclear image data can be represented as list mode data, the corresponding image data determination unit can be adapted to sort the list mode data in accordance with the determined motion states. For instance, all parts of the list mode data that have been acquired during one or more time intervals of a motion state are provided together in the list mode data and marked as belonging to the respective motion state.

In a preferred embodiment, the corresponding image data determination unit is adapted to determine for each motion state one or more time intervals during which the region of interest was in a state corresponding to the motion state during the acquisition of the nuclear image data based on the motion signal and further to determine the nuclear image data corresponding to a motion state based on whether the nuclear image data has been acquired during the one or more time intervals of the respective motion state. In an embodiment, the corresponding image data determination unit can be adapted to determine the time intervals for each motion state by providing a representation of the motion signal to a user such that a user can indicate the time intervals for each motion state. Moreover, the corresponding image data determination unit can also be a receiving unit receiving the time intervals for each motion state, for instance, from a storage device or from a user. Further, the corresponding image data determination unit can be adapted to determine the time intervals for each motion state based on known characteristics of the motion signal that are indicative for the motion state. For instance, if for a specific motion state it is known that the motion signal lies above a certain threshold, the corresponding image data determination unit can determine all time intervals showing a motion signal above the threshold as belonging to the motion state. Moreover, if it is determined that the motion state is only being adopted at a very short time period or even only for one moment in time, the corresponding image data determination unit can be adapted to determine a predetermined shortest time interval around this moment as the time interval corresponding to the motion state. The shortest time interval can be predetermined based on the desired accuracy of the image, on pre-knowledge on the expected movement of the region of interest, on the resolution of the motion signal, etc. Moreover, the corresponding image data determination unit can be adapted to adapt the shortest time interval automatically based, for instance, on the rate of change of the region of interest, or a velocity of a part of the region of interest.

If a motion state has occurred at more than one time interval during the acquisition of the nuclear image data, the time intervals for the motion state can be determined, for instance, based on the motion signal. For example, if different time intervals of the motion signal show the same motion pattern referring to a specific motion state, then all of these time intervals can be determine as showing this specific motion state. In this context a same motion pattern might be defined, for instance, by two time intervals showing a difference below a predetermined threshold. The threshold might be determined, for instance, based on an expected scale of movement in the region of interest, based on an expected accuracy of the motion signal, etc. Moreover, time intervals referring to a motions state can also be determined using pre-knowledge of the characteristic motion signal of this motion state. For example, if the motion state is an exhalation state of the lung of the patient, it can be known that a position signal, i.e. motion signal, in this state is nearly constant for a certain time period around a local minimum of the motion signal.

In particular, if the motion signal is indicative of a regular periodic or cyclic motion, the motion states of each period or cycle will be repeated. Accordingly, the corresponding image data determination unit can be adapted to determine a time interval corresponding to a specific repeated motion state in each of the periods or cycles. However, if during the acquisition of the nuclear image data the periodic motion state has changed, for instance, due to a large scale change of position of the patient, other motion states might be identified in the periodic motion following the change of position.

If the nuclear image data can be represented as list mode data, the corresponding image data determination unit can be adapted to sort the list mode data in accordance with the determined motion states, for instance, all parts of the list mode data that have been acquired during one or more time intervals of a motion state are provided together in the list mode data and marked as belonging to the respective motion state.

The absorption map reconstruction unit is then adapted to reconstruct an absorption map for each motion state based on the corresponding nuclear image data of the respective motion state. An absorption map is indicative of an absorption of nuclear radiation in the region of interest. In particular, an absorption map provides for each part of the region of interest, for instance, for each pixel or voxel of the region of interest, a value that is indicative of an absorption of radiation in this part of the region of interest. The absorption of radiation in a part of a region of interest is further indicative for the density of the material in this part. The absorption map reconstruction unit can be adapted for reconstructing the absorption map for each motion state based on the corresponding nuclear image data by solving or approximating the exponential X-ray transform for the nuclear image data.

In a preferred embodiment, the absorption map reconstruction unit is adapted to reconstruct the absorption map for a motion state using a machine learning algorithm. In particular, the absorption map reconstruction unit can be adapted to solve the exponential X-ray transform using a machine learning algorithm. Preferably, the machine learning algorithm refers to a trained neural network, in particular, a generative adversarial network. Such a machine learning algorithm can be trained, for instance, by providing a plurality of nuclear image data sets for different cases and correspondingly known absorption maps for the different cases, for instance, acquired using an X-ray CT imaging system, as input and desired output to the neural network in training. The neural network can then be trained to determine corresponding absorption maps also for other nuclear image data sets. An example for a method for providing a machine learning algorithm for determining an absorption map from nuclear image data is provided by the article "MedGAN: Medical Image Translation using GANs", by K. Armanious et al., Computerized Medical Imaging and Graphics, volume 79, (2019). Since the absorption map is determined for each determined motion state based on the nuclear image data and not, for instance, based on X-ray CT image data, the absorption map very accurately reflects the position of the region of interest during the respective motion state at which the nuclear image data has been acquired.

In a preferred embodiment, the absorption map corresponds to a pseudo CT image, wherein the absorption information provided by the pseudo CT image corresponds to the absorption information provided by a CT image acquired during a CT imaging procedure. Preferably, the absorption information provided by a pseudo CT image refers to providing the absorption information on the same scale, i.e. using the same values, as provided by a CT image. In particular, the absorption map reconstruction unit can be adapted to scale the reconstructed absorption maps accordingly. Alternatively, if a machine learning algorithm is used for reconstructing the absorption map, the machine learning algorithm can be trained by using CT images of a region of interest such that the trained machine learning algorithm will provide corresponding pseudo CT images as output when provided with nuclear image data as input.

The nuclear image reconstruction unit is adapted to reconstruct one or more nuclear images of the region of interest based on the nuclear image data and the absorption maps reconstructed for each motion state from the nuclear image data. For instance, the nuclear image reconstruction unit can be adapted to reconstruct one or more nuclear images of the region of interest using known reconstruction algorithms for nuclear image data being corrected using absorption data, like X-ray CT image data.

In a preferred embodiment, the nuclear image reconstruction unit is adapted to reconstruct an absorption corrected nuclear image for each motion state based on the corresponding nuclear image data and the absorption map. In this case, the absorption corrected nuclear images for each motion state can be provided as 4D nuclear image set to a user. Moreover, in an embodiment, the nuclear image reconstruction unit can be adapted to reconstruct a motion corrected nuclear image based on the nuclear image data and the absorption maps for each motion state. For instance, the nuclear image reconstruction unit can be adapted to use the absorption corrected nuclear images for each motion state and register the absorption corrected nuclear images for each motion state to each other to reconstruct a motion corrected nuclear image based on the registered absorption corrected nuclear images. Alternatively, in an embodiment, the nuclear image reconstruction unit can be adapted to register the absorption maps of each motion state to each other and to use the registration for registering the nuclear image data to one of the motion states in order to reconstruct the motion corrected nuclear image. Since the absorption maps are reconstructed based on the nuclear image data, the registration of the absorption maps directly provides the registration of the nuclear image data from which the absorption maps have been reconstructed. Thus, this embodiment allows a very easy reconstruction of a motion corrected nuclear image.

Moreover, the nuclear image reconstruction unit can further be adapted to register high-resolution CT image data, for instance, pre-procedural high-resolution CT image data, with the absorption maps and to use the registered high-resolution CT image data for the reconstruction of the one or more nuclear images. Since the absorption maps are indicative for the absorption of radiation in the region of interest and thus contain substantially the same information as an X-ray CT image, the registration between high-resolution CT image data and the absorption maps is very easy using known registration algorithms. Moreover, since the absorption maps very accurately reflect the state of the region of interest during the respective motion state, also the registered high-resolution CT image data reflects the motion states of the region of interest very well, although they have not been acquired, for instance, during the same motion state or even in the same time period as the acquisition of the nuclear image data. Using then the registered high-resolution CT image data for the reconstruction of the one or more nuclear images allows for even more accurate motion and attenuation correction of the resulting one or more nuclear images. Preferably, an elastic registration algorithm is used for registering the absorption maps to each other or to the high-resolution CT image data.

In another aspect of the present invention, a nuclear imaging system is presented, wherein the nuclear imaging system comprises a) a detector for detecting nuclear events in a field of view of the detector and to determine nuclear image data of a region of interest of a patient based on the detected nuclear events, b) an apparatus as described above for providing one or more nuclear images. Preferably, the nuclear imaging system is a PET or SPECT imaging system, wherein the detector is adapted to detect gamma radiation originating from the region of interest of a patient.

In further aspect of the invention, a method for providing a nuclear image of a region of interest of a patient is presented, wherein the method comprises a) providing nuclear image data of a region of interest of a patient acquired using a nuclear imaging device, b) providing a motion signal indicative of a motion of the region of interest of the patient during an acquisition of the nuclear image data, c) determining different motion states of the region of interest based on the motion signal, wherein each of the different motion states is indicative for a different state of the region of interest, d) determining for each motion state nuclear image data corresponding to the motion state, wherein nuclear image data corresponds to a motion state if the nuclear image data has been acquired during a state of the region of interest corresponding to the motion state, e) reconstructing an absorption map for each motion state based on the corresponding nuclear image data of the respective motion state, wherein the absorption map is indicative of an absorption of nuclear radiation in the region of interest, and f) reconstructing one or more nuclear images of the region of interest based on the nuclear image data and the absorption maps reconstructed for each motion state.

In another aspect of the invention, a computer program for providing a nuclear image of a region of interest is presented, wherein the computer program comprises program code means for causing the apparatus as described above to carry out the steps of the method as described above when the computer program is executed by the apparatus.

It shall be understood that the apparatus of claim 1, the system of claim 13, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereafter.

BRIEF DESCRIPTION OF THE DRAWINGS

In the following drawings:

FIG. 3 shows a flowchart exemplarily illustrating an embodiment of a method for providing a nuclear image of a region of interest according to the invention.

DETAILED DESCRIPTION OF EMBODIMENTS

Figure 1:
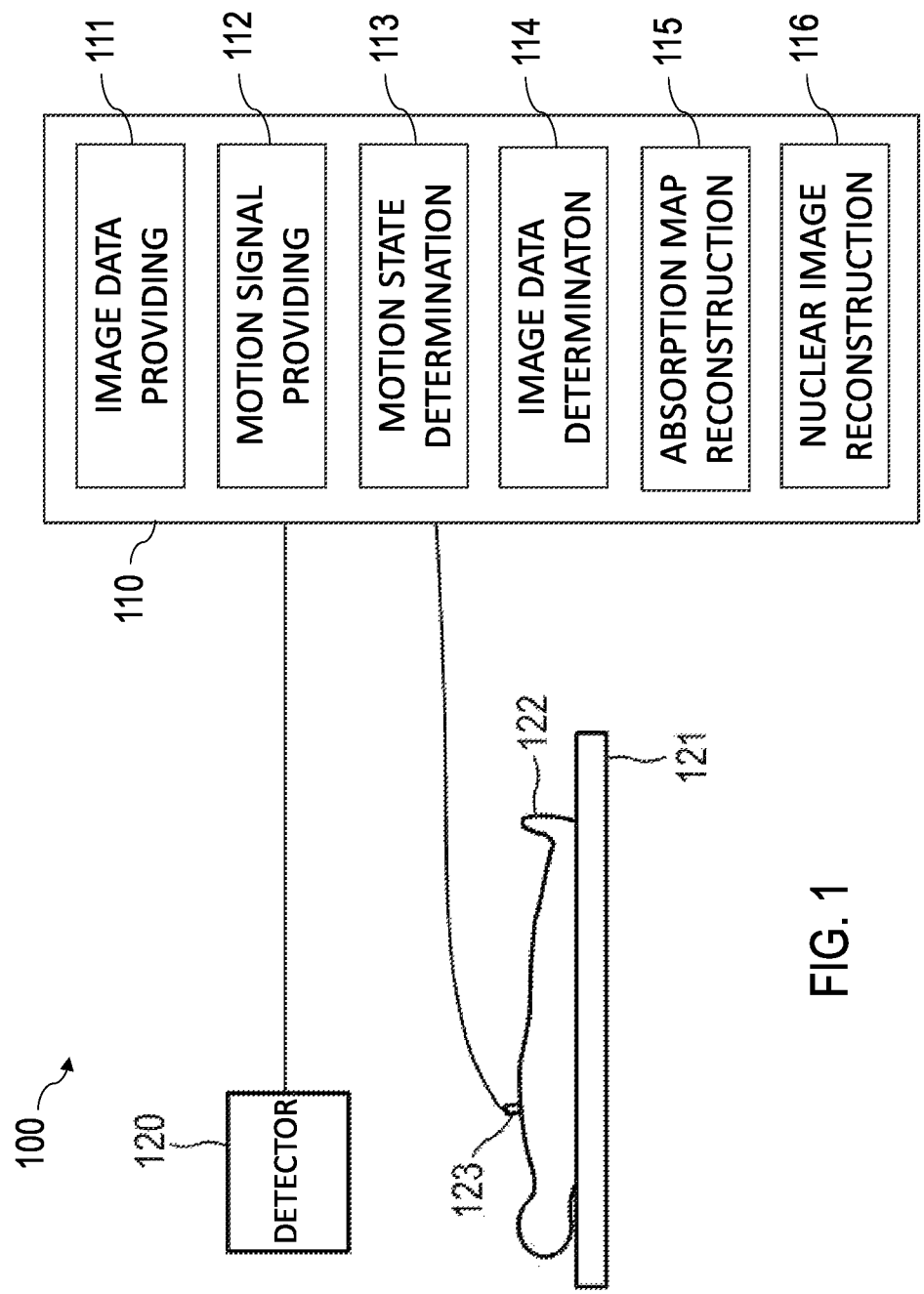
FIG. 1 shows schematically and exemplarily an embodiment of a nuclear imaging system according to the invention.

FIG. 1 shows schematically and exemplarily an embodiment of a nuclear imaging system comprising an apparatus for providing a nuclear image of a region of interest of a patient according to the invention. In the following embodiment, the nuclear imaging system 100 comprises a detector 120 for detecting nuclear events in a field of view of the detector 120. The nuclear imaging system 100 can be a PET imaging system and the detector 120 can be a gamma radiation detector as used in a PET imaging system. In particular, the field of view of the detector 120 comprises a region of interest of a patient 122 lying on a patient table 121. The patient 122 has been injected with a radioactive substance in form of a radiopharmaceutical comprising, for instance, Fluorine-18. In case of a PET or SPECT imaging procedure the radiopharmaceutical will be chosen such that it emits a positron, wherein the positron after annihilation with an electron will provide two gamma photons moving in opposite directions. The detector 120 can be adapted to detect one or both of the gamma photons resulting from the annihilation, i.e. the nuclear event, in the region of interest. If the nuclear imaging system 100 refers to a PET detector the detector 120 is adapted to detect both photons and to provide the detection of the photons in a form of list mode data as nuclear image data. The nuclear imaging system 100 further comprises an apparatus 110 for providing a nuclear image of the region of interest of the patient 120.

The apparatus 110 comprises a nuclear image data providing unit 111, a motion signal providing unit 112, a motion state determination unit 113, a corresponding image data determination unit 114, an absorption map reconstruction unit 115 and a nuclear image reconstruction unit 116.

In this embodiment, the nuclear image data providing unit 111 is a receiving unit for receiving the nuclear image data of the detector 120 and for providing the received nuclear image data. In this example, the nuclear image data refers to PET image data acquired by the PET imaging system 100. However, in other embodiments the nuclear image data can refer, for instance, to SPECT data, or to any other kind of nuclear image data acquired using a nuclear imaging system. The nuclear imaging data has been acquired by the detector 120 during a predetermined time period, for instance, a time period lying between a few minutes and an hour based on the size of the region of interest.

The motion signal providing unit 112 is in this embodiment adapted to provide as motion signal a signal acquired using a motion sensor 123 attached to the chest of the patient. The motion signal is in this case indicative for a breathing motion of the chest region of the patient during the acquisition of the nuclear image data. The motion signal can be provided in form of an accelerometer signal indicating the acceleration of the sensor 123 during the breathing of the patient, or can be provided as a position signal indicative of the position of the sensor 123 during the breathing of the patient. Generally, the motion signal refers to a sequence of measurement values in time, for instance, to a sequence of positions of the motion sensor 123 with time, or to a sequence of acceleration values measured by the motion sensor 123 with time.

Based on the provided motion signal of the motion signal providing unit 112, the motion state determination unit 113 is adapted to determine different motion states of the region of interest based on the motion signal. Since in this case the provided motion signal is indicative of a breathing motion of the patient 122, the motion state determination unit 113 is adapted to determine different breathing states of the breathing cycle of the patient 122 based on the motion signal. For instance, the motion state determination unit is adapted to determine based on the motion signal a first and a second substantially motionless state as first and second motion states, wherein the first and the second motion states refer to an exhalation state and an inhalation state of the lung of the patient 122, respectively. Since during the maximal inhalation state and the maximal exhalation state for a short time period the patient is substantially motionless, the motion state determination unit can be adapted to search for parts of the motion signal that indicate such a substantially motionless state of the region of interest of the patient 122. For example, if the motion signal provided by the motion sensor 123 refers to an acceleration of the motion sensor 123, the motion state determination unit can be adapted to search for the parts of the motion signal in which the acceleration is substantially zero and determine such parts as motion states in which the patient is substantially motionless.

In another example, if the motion signal provided by the motion signal providing unit refers to a position of the sensor 123, the motion state determination unit can be adapted to search for parts of the motion signal in which the rate of change of the position of the sensor is substantially zero, i.e. in which the position of the sensor is substantially constant. In this context, the term "substantially" always refers to deviations being lower that a predetermined threshold, wherein the threshold can be defined based on the application, for instance, based on the expected quality of the signal, the expected movement of the patient, the still acceptable deviations, etc. Based on the provided motion signal, also some filters like averaging filters can be provided to avoid measurement inaccuracies in the motion signal when determining the different motion states. Moreover, the motion state determination unit 113 can be adapted to also determine motion states that lie in between the first and the second motion state, i.e. in between an exhalation state and an inhalation state of the lung of the patient 122, as motion states.

After the motion state determination unit has determined the motion states in the motion signal, for instance, has determined the maximal exhalation and inhalation states of the patient 122 in the motion signal as motion states, the motion state determination unit can be adapted to present the result of this determination on a display to a user. The user can then check the result of the determination, for instance, can check if the motion state determination unit has correctly determined the breathing motion states and can then confirm, amend or reject the result of the determination of the motion state determination unit using, for instance, an input unit like a keyboard or a computer mouse. In other embodiments, the motion state determination unit 113 can be adapted to determine the different motion states in an interaction with the user, for instance, by providing the motion signal to a user using, for instance, a display, and by receiving the determined motion states from the user using, for instance, an input unit like a keyboard or mouse.

Since the breathing motion is a regular and in particular a cyclic motion, the body of the patient 122 will repeat the same motion states for each breathing cycle, wherein each motion state refers to a specific state, for instance, position, of the region of interest of the patient 122.

The corresponding image data determination unit 114 then determines for each motion state the nuclear image data corresponding to the motion state. In particular, the corresponding image data determination unit 114 can be adapted to determine whether a nuclear image data has been acquired during a time period in which the patient was in a respective motion state during the acquisition of the nuclear image data. For instance, the corresponding image data determination unit 114 can be adapted to determine all time intervals in which the patient was in a specific motion state during the acquisition of the nuclear image data based on the motion signal. In an example, the corresponding image data determination unit 114 can be adapted to use pre-known characteristics of a motion signal referring to a specific motion state. In the present example, the corresponding image data determination unit 114 is adapted to determine all time intervals in which the patient was in the first motion state, i.e. the exhalation state, and all time intervals in which the patient was in the second motion state, i.e. the inhalation state. The corresponding image data determination unit 114 is then adapted to determine which nuclear image data was acquired during the time intervals referring to the first and the second motion states, for instance, based on time stamps provided for each detected event in the nuclear image data.

If the nuclear image data refers to list mode data, the corresponding image data determination unit 114 can be adapted to sort the list mode data in accordance with the determined motion states. The sorted list mode data, i.e. the corresponding nuclear image data, can then be provided, for instance, in form of a table or list linking the parts of the nuclear image data to the motion state to which they correspond. If the motion signal is indicative of a regular, in particular periodic motion like breathing motion of the patient 122, the same motion states can be identified in each cycle of the periodic motion and the corresponding nuclear image data can then be linked to the motion state, for instance, in form of a table.

The absorption map reconstruction unit 115 then reconstructs an absorption map for each motion state based on the corresponding nuclear image data of the respective motion state. In particular, if the motion is a periodic motion like breathing motion, the nuclear image data from all cycles of the periodic motion corresponding to the specific motion state that is repeated during the periodic motion can be used for reconstructing an absorption map for this motion state of the periodic motion. However, in other embodiments, if the motion is not a periodic motion or comprises irregularities, some of the motion states might not be repeated such that these motion state refers to a unique state of the region of interest and thus only the nuclear image data acquired during the time period of this unique state can be used for reconstructing the absorption map.

In an example, the absorption map reconstruction unit 115 uses a trained neural network, in particular, a generative adversarial network, to reconstruct an absorption map for a motion state based on the corresponding nuclear image data. The trained neural network can be trained, for instance, before the application to the nuclear image data by providing a plurality of nuclear image data sets to the neural network together with the desired output for these nuclear image data sets, i.e. together with X-ray CT images defining the attenuation of the region of interest that has been imaged with the nuclear image data sets. In this case, after the training phase the trained neural network will provide based on nuclear image data a corresponding pseudo CT image as absorption map which represents absorption information of the region of interest imaged by the nuclear imaging system in the same way as a normal X-ray CT image would provide.

The nuclear image reconstruction unit 116 then reconstructs, for instance, for each motion state of a breathing cycle, an attenuation corrected nuclear image based on the nuclear image data and the determined absorption maps. The attenuation correction and reconstruction of the nuclear image data can be based on known reconstruction methods that use, for instance, normally generated X-ray CT image data. Additionally or alternatively, the nuclear image reconstruction unit 116 can also reconstruct a motion corrected nuclear image by registering the absorption maps to each other and by using this registration to also register the nuclear image data to each other, i.e. to correct the nuclear image data from any motion. Thus, a nuclear image reconstructed from the registered nuclear image data can be regarded as the motion corrected nuclear image. During the reconstruction of the motion corrected nuclear image, the nuclear image reconstruction unit 116 can also be adapted to use the registered absorption maps to also correct the reconstructed nuclear image for attenuation.

If additionally high resolution CT image data has been acquired of the patient 122, for instance, before the acquisition of then nuclear image data, the absorption maps can also be used to register the pre-procedural high-resolution CT image data to each of the absorption maps, i.e. to adapt the pre-procedural high-resolution CT image data to each motion state. The nuclear image reconstruction unit 116 can then also use the pre-procedural high-resolution CT image data that has been registered to the absorption maps for attenuation correction of the nuclear image data during the reconstruction of the nuclear image or as overlay for presenting the nuclear image data in the context of the anatomical structures visible in the pre-procedural high-resolution CT image data.

Figure 2:
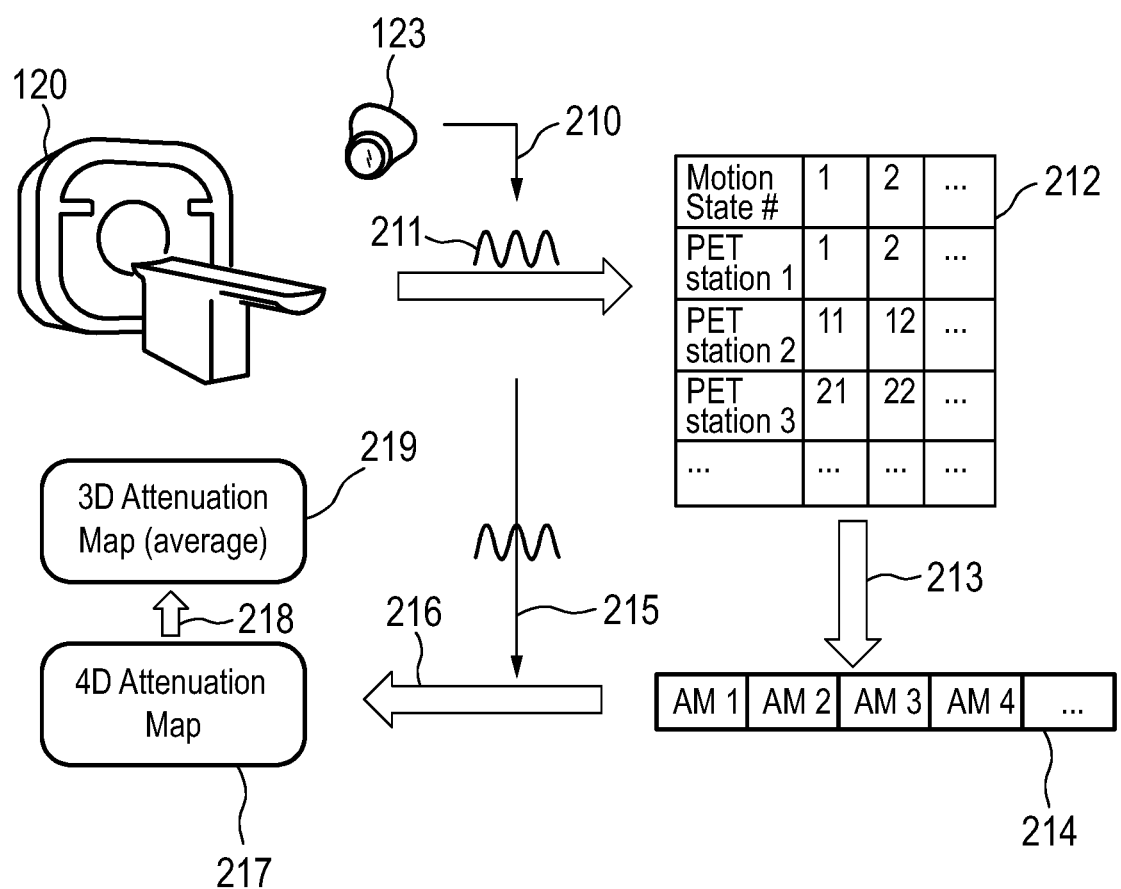
FIG. 2 shows a schematically and exemplary a workflow for reconstructing a nuclear image based on the principles underlying the invention.

FIG. 2 shows a process for reconstructing one or more nuclear images according to the principles of the invention. In this example, as indicated by the PET imaging system 120 shown in FIG. 2, firstly PET imaging data is acquired. In this embodiment, the patient is monitored by a camera 123 providing 210 a motion signal 211, for instance, by analyzing the monitoring images for changes in a region of interest. The PET imaging data is then sorted in accordance with identified motion states in the motion signal 211 as indicated by the table 212 shown in FIG. 2. Based on this sorted PET image data, as represented by table 212, for each motion state a respective attenuation map 214, as indicated by AM1, AM2, AM3, AM4, etc., is determined 213 based on the PET image data. Using 215 the provided motion signal 211, the attenuation maps 214 can be assembled 216 into a 4D attenuation map 217. The 4D attenuation map 217 can then directly be used for reconstructing one or more nuclear images or can in a step 218 be averaged to a 3D attenuation map 219 which can then also be used for reconstructing a nuclear image.

FIG. 3 shows a flowchart exemplarily illustrating an embodiment of a method for providing a nuclear image of a region of interest of a patient 122. The method 300 comprises a first step 310 of providing nuclear image data of a region of interest of a patient 122, wherein the nuclear image data has been acquired using, for instance, the nuclear imaging system 100. In a step 311, a motion signal indicative of a motion of the region of interest of the patient 122 is provided, for instance, by receiving a motion signal from motion sensor 123. In the method 300, the steps 310 and 311 of providing the nuclear image data and providing a motion signal, respectively, can be processed in any arbitrary sequence or at the same time.

In a next step 312, different motion states of the region of interest are determined based on the motion signal, wherein each of the different motion states is indicative for a different state of the region of interest, preferably a different substantially motionless state of the region of interest. The step of determining the motion states can also refer to a step of providing the motion states, for instance, based on already stored motion states or motion states received from a user input. Based on the different motion states, in step 313 nuclear image data corresponding to each motion state is determined. The nuclear image data corresponds to a motion state if the nuclear image data has been acquired during the same state of the region of interest to which the motion state refers. In step 314, an absorption map is reconstructed, for instance, using a trained neural network, for each motion state based on the corresponding nuclear image data of the respective motion state. The absorption maps are indicative of the absorption of nuclear radiation in the region of interest. In a last step 315, one or more nuclear images are reconstructed of the region of interest based on the nuclear image data and the absorption maps reconstructed for each motion state.

Hybrid PET/CT imaging is an established clinical modality combination in nuclear medicine, since the CT images both allow to correct the PET image data for image degrading effects, such as photon attenuation and scatter, and to provide a layover allowing for anatomical localization of features in the PET images. Typical PET image data acquisition times do not allow to avoid regular body motion, such as breathing, while CT image data acquisition is sufficiently short, which results in a spatial mismatch between the CT and PET images.

To overcome this problem, it is suggested in an embodiment of the invention recovering pseudo CT images from the PET image data alone. In particular, artificial-intelligence-based methods allow to provide such pseudo CT images with a sufficient image quality for image artefact correction and anatomical localization. Further, this invention adds, for instance, the time domain to the pseudo CT images, i.e. by recovering not a single, but a time series of pseudo CT images. When PET coincidence data as nuclear image data are acquired in list mode, each entry carries the detection time stamp, allowing separation of data by time intervals. The resulting time-series pseudo CT images or a derived average of these images better matches the body motion states during the PET image data acquisition and provide better matching anatomical localization overlays to the PET images.

For solving the problem of the exponential X-ray transform, i.e. recovering the absorption map of a body from the acquired PET image data, approximate solutions to the problem are known. Moreover, generative adversarial networks can be used to recover absorption information, i.e. absorption maps, based on patient PET image data and the corresponding CT image data. Since PET image data acquisition is more time-intensive, multiple breathing cycles are usually covered by an acquisition. Thus, deriving a solution for the time-dependent exponential X-ray transform is of interest to provide accurate attenuation correction for the PET image data.

It is known, for instance, that breathing motion correction in PET image data can be achieved via external breathing sensors and breathing gating, including, for example, approaches like 4D breathing CT imaging to correct the motion in the PET image data and to provide accurate time dependent absorption correction and anatomic localization. However, a breathing signal can also be derived directly from the PET list mode data, i.e. the PET image data. Moreover, it is even more accurate to determine the entire spatial motion pattern directly from the PET image data itself.

To perform a time-dependent estimation of the exponential X-ray transform it is suggested in this invention to generate pseudo 4D CT image data from the PET image data, for instance, using neural networks. Further, an estimate for the motion during the PET image data acquisition can be derived from the resulting pseudo 4D CT image data. This estimate can then be used, for instance, in order to correct the motion during the PET image data acquisition and enable accurate registration to previously acquired high-resolution CT image data.

In one embodiment, a process is suggested for realizing the invention, comprising a first step of setting up a PET scanner and acquiring PET image data for a moving part of the patient, for instance, the thorax or abdomen. In a next step applying a hardware- or software-based approach to detect the patient's motion or breathing signal. In a further step the PET list mode data, i.e. PET image data, is sorted according to a derived trigger, for instance, a breathing signal, with respect to different motion states of the patient during the acquisition. In a last step a reconstruction method, for instance, a trained neural network, can be used to reconstruct absorption maps like pseudo CT image data per time step from the acquired PET image data.

The generated pseudo 4D CT image data represents the motion during the PET image data acquisition and can be used for time-dependent absorption correction and anatomic localization. In addition, it can be used to spatially co-register pre-procedural high-resolution CT image data, for instance, with an elastic registration, and to thus integrate high-quality CT image data into the absorption correction and anatomy localization.

Although in the above embodiments the nuclear imaging system is a PET imaging system, in other embodiments the nuclear imaging system can also be a SPECT imaging system.

Although in the above embodiments the motion signal is provided based on the signal of a motion sensor as acceleration signal or position signal, in other embodiments the motion signal can also be provided by analyzing monitoring images of a monitoring camera monitoring a patient during the nuclear imaging data acquisition. Moreover, in another embodiment, the motion signal can be determined by the motion signal providing unit based on the nuclear image data itself, in particular, by identifying motion in the region of interest in the nuclear image data itself.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the providing of the nuclear image data, the providing of a motion signal, the determination of different motion states, the determination of corresponding nuclear image data, the reconstruction of an absorption map and the reconstructing of one or more nuclear images, performed by one or several units or devices can be performed by any other number of units or devices. For instance, these procedures can be carried out by a single device. These procedures can be implemented as computer program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention refers to an apparatus that allows to improve the image quality of nuclear images, e.g. PET images. The apparatus comprises a providing unit for providing nuclear image data of a region of interest, a providing unit for providing a motion signal indicative of a motion of the region of interest, a determination unit for determining different motion states of the region of interest based on the motion signal, a determination unit for determining for each motion state nuclear image data corresponding to the motion state, a reconstruction unit for reconstructing an absorption map for each motion state based on the corresponding nuclear image data of the respective motion state, and a reconstruction unit for reconstructing one or more nuclear images of the region of interest based on the nuclear image data and the absorption maps reconstructed for each motion state.

The invention claimed is:

1. An apparatus for providing a nuclear image of a region of interest of a patient, wherein the apparatus comprises:
   a nuclear image data providing unit for providing nuclear image data of a region of interest of a patient acquired using a nuclear imaging device,
   a motion signal providing unit for providing a motion signal indicative of a motion of the region of interest of the patient during an acquisition of the nuclear image data,
   a motion state determination unit for determining different motion states of the region of interest based on the motion signal, wherein each of the different motion states is indicative for a different state of the region of interest,
   a corresponding image data determination unit for determining for each motion state nuclear image data corresponding to the motion state, wherein nuclear image data corresponds to a motion state if the nuclear image data has been acquired during a state of the region of interest corresponding to the motion state,
   an absorption map reconstruction unit for reconstructing an absorption map for each motion state based on the corresponding nuclear image data of the respective motion state, wherein the absorption map is indicative of an absorption of nuclear radiation in the region of interest, and
   a nuclear image reconstruction unit for reconstructing one or more nuclear images of the region of interest based on the nuclear image data and the absorption maps reconstructed for each motion state.

2. The apparatus according to claim 1, wherein the absorption map reconstruction unit is adapted to reconstruct the absorption map for a motion state using a machine learning algorithm.

3. The apparatus according to claim 2, wherein the machine learning algorithm refers to a trained neural network.

4. The apparatus according to claim 1, wherein an absorption map corresponds to a pseudo CT image, wherein the absorption information provided by the pseudo CT image corresponds to the absorption information provided by a CT image acquired during an x-ray CT imaging procedure.

5. The apparatus according to claim 1, wherein the corresponding image data determination unit is adapted to determine for each motion state one or more time intervals during which the region of interest was in a state corresponding to the motion state during the acquisition of the nuclear image data based on the motion signal and further to determine the nuclear image data corresponding to a motion state based on whether the nuclear image data has been acquired during the one or more time intervals of the respective motion state.

6. The apparatus according to claim 1, wherein the motion signal providing unit is adapted to determine the motion signal based on the nuclear image data.

7. The apparatus according to claim 5, wherein the motion signal providing unit is adapted to provide as motion signal a signal of a sensor configured to detect a motion of the region of interest of the patient.

8. The apparatus according to claim 1, wherein the motion signal is indicative of a regular body motion in the region of interest of the patient.

9. The apparatus according to claim 1, wherein the nuclear image reconstruction unit is adapted to reconstruct an absorption corrected nuclear image for each motion state based on the corresponding nuclear image data and the absorption maps or wherein the nuclear image reconstruction unit is adapted to reconstruct a motion corrected nuclear image based on the nuclear image data and the absorption maps for each motion state.

10. The apparatus according to claim 9, wherein the nuclear image reconstruction unit is adapted to register the absorption maps of each motion state to each other and to use the registration for registering the nuclear image data to one of the motion states in order to reconstruct the motion corrected nuclear image.

11. The apparatus according to claim 1, wherein the nuclear image data refers to PET image data or SPECT image data.

12. A nuclear imaging system comprising:
 a detector for detecting nuclear events in a field of view of the detector and to determine nuclear image data of a region of interest of a patient based on the detected nuclear events,
 an apparatus according to claim 1.

13. A method for providing a nuclear image of a region of interest of a patient, wherein the method comprises:
 providing nuclear image data of a region of interest of a patient acquired using a nuclear imaging device,
 providing a motion signal indicative of a motion of the region of interest of the patient during an acquisition of the nuclear image data,
 determining different motion states of the region of interest based on the motion signal, wherein each of the different motion states is indicative for a different state of the region of interest,
 determining for each motion state nuclear image data corresponding to the motion state, wherein nuclear image data corresponds to a motion state if the nuclear image data has been acquired during a state of the region of interest corresponding to the motion state,
 reconstructing an absorption map for each motion state based on the corresponding nuclear image data of the respective motion state, wherein the absorption map is indicative of an absorption of nuclear radiation in the region of interest, and
 reconstructing one or more nuclear images of the region of interest based on the nuclear image data and the absorption maps reconstructed for each motion state.

14. A computer program for providing a nuclear image of a region of interest, wherein the computer program comprises program code means for causing the apparatus to carry out the steps of the method as defined in claim 13 when the computer program is executed by the apparatus.

15. The method according to claim 13, reconstructing an absorption map for each motion state includes use of a machine learning algorithm.

16. The method according to claim 15, wherein the machine learning algorithm refers to a trained neural network.

17. The method according to claim 13, wherein the absorption map corresponds to a pseudo CT image, wherein the absorption information provided by the pseudo CT image corresponds to the absorption information provided by a CT image acquired during an x-ray CT imaging procedure.

18. The method according to claim 13, further comprising determining for each motion state of the region of interest, one or more time intervals during which the region of interest was in a state corresponding to the motion state during the acquisition of the nuclear image data based on the motion signal, and wherein determining the nuclear image data corresponding to a motion state is based on whether the nuclear image data has been acquired during the one or more time intervals of the respective motion state.

19. The method according to claim 18, wherein the motion signal is a signal of a sensor configured to detect a motion of the region of interest of the patient.

20. The method according to claim 13, wherein determining the motion signal is based on the nuclear image data.

21. The method according to claim 13, further comprising reconstructing an absorption corrected nuclear image for each motion state based on the corresponding nuclear image data and the absorption maps or reconstructing a motion corrected nuclear image based on the nuclear image data and the absorption maps for each motion state.

* * * * *